(12) United States Patent
Azimi

(10) Patent No.: US 9,247,004 B2
(45) Date of Patent: Jan. 26, 2016

(54) SYSTEM AND METHOD FOR RELIABLE AND SCALABLE HEALTH MONITORING

(75) Inventor: Saeed Azimi, Los Gatos, CA (US)

(73) Assignee: VITAL CONNECT, INC., Campbell, CA (US)

( * ) Notice: Subject to any disclaimer, the term of this patent is extended or adjusted under 35 U.S.C. 154(b) by 772 days.

(21) Appl. No.: 13/281,153

(22) Filed: Oct. 25, 2011

(65) Prior Publication Data

US 2013/0099936 A1    Apr. 25, 2013

(51) Int. Cl.
| | |
|---|---|
| A61B 5/00 | (2006.01) |
| H04L 29/08 | (2006.01) |
| G06F 17/30 | (2006.01) |
| A61B 5/11 | (2006.01) |
| G06F 19/00 | (2011.01) |

(52) U.S. Cl.
CPC .............. *H04L 67/12* (2013.01); *A61B 5/1113* (2013.01); *G06F 17/3056* (2013.01); *G06F 19/3412* (2013.01); *H04L 67/142* (2013.01); *A61B 5/0002* (2013.01); *A61B 5/0024* (2013.01); *A61B 5/6833* (2013.01); *A61B 2560/045* (2013.01); *A61B 2560/0412* (2013.01); *G06F 19/34* (2013.01)

(58) Field of Classification Search
CPC ............ G06F 19/322; G06F 17/30557; G06F 17/3056; G06F 19/3418; G06F 9/54; G06F 11/0709; A61B 5/0002; A61B 5/1113; G06Q 50/22; H04L 67/142
USPC ....... 340/870.01; 705/2; 707/999.1; 709/217, 709/227; 719/319, 321
See application file for complete search history.

(56) References Cited

U.S. PATENT DOCUMENTS

| | | | |
|---|---|---|---|
| 5,752,917 | A | 5/1998 | Fuchs |
| 6,393,341 | B1 | 5/2002 | Lawrence et al. |
| 2004/0167465 | A1 | 8/2004 | Mihai et al. |
| 2006/0122864 | A1* | 6/2006 | Gottesman et al. ............... 705/2 |
| 2006/0230124 | A1 | 10/2006 | Belfiore et al. |
| 2006/0293571 | A1 | 12/2006 | Bao et al. |
| 2007/0174716 | A1 | 7/2007 | Erdtmann et al. |
| 2008/0097909 | A1 | 4/2008 | Dicks et al. |

(Continued)

FOREIGN PATENT DOCUMENTS

| | | |
|---|---|---|
| CN | 1151857 | 6/1997 |
| CN | 2544684 | 4/2003 |

(Continued)

OTHER PUBLICATIONS

PCT International Search Report and Written Opinion of the International Searching Authority, issued Jan. 8, 2013, application No. PCT/US2012/061838.

*Primary Examiner* — Steven Lim
*Assistant Examiner* — Benyam Haile
(74) *Attorney, Agent, or Firm* — Sawyer Law Group, P.C.

(57) ABSTRACT

A health-monitoring system and method are disclosed. The health-monitoring system and method comprise a sensory system and a sensory to front-end communication (SFCM) protocol coupled to the sensory system. The health-monitoring system and method include a front-end system coupled to the sensory system and a front-end to back-end communication (FBCM) protocol coupled to the front-end system. The health-monitoring system and method include a back-end system. The SFCM protocol communicates with the front-end system using a first state awareness link and the FBCM protocol communicates with the back-end system using a second state awareness link.

20 Claims, 2 Drawing Sheets

(56) References Cited

U.S. PATENT DOCUMENTS

| | | |
|---|---|---|
| 2009/0054737 A1 | 2/2009 | Magar et al. |
| 2009/0058635 A1* | 3/2009 | LaLonde et al. ......... 340/539.11 |
| 2009/0115628 A1 | 5/2009 | Dicks et al. |
| 2009/0119658 A1 | 5/2009 | Thoon et al. |
| 2010/0049006 A1 | 2/2010 | Magar et al. |
| 2010/0056875 A1 | 3/2010 | Schoenberg et al. |
| 2010/0076412 A1 | 3/2010 | Rush et al. |
| 2011/0178499 A1* | 7/2011 | Brukalo et al. ............... 604/504 |
| 2012/0302841 A1* | 11/2012 | Coressel et al. .............. 600/301 |
| 2013/0045685 A1 | 2/2013 | Kiani |

FOREIGN PATENT DOCUMENTS

| | | |
|---|---|---|
| JP | 2011-502369 | 1/2011 |
| WO | WO0198936 | 12/2001 |
| WO | WO2006/111878 | 10/2006 |

* cited by examiner

SYSTEM AND METHOD FOR RELIABLE AND SCALABLE HEALTH MONITORING

FIELD OF THE INVENTION

The present invention relates to health monitoring, and more particularly, to a system and method for reliable and scalable health monitoring.

BACKGROUND

Monitoring systems are used in a variety of applications including monitoring the health of individuals. Conventional health monitoring systems typically include a combination of underlying systems or device components such as sensors, recording systems, and storage units. Software is integrated with the hardware of each device component to aid the communication of data between each device component of the conventional health monitoring system.

These conventional health monitoring systems typically have predetermined hardware and software architectures for each device component. However, if one of these device components is either updated with new hardware or replaced with a different device component, the communication of data is disrupted and the software integrated with the hardware of each device component must be updated to match the new underlying device configuration of the conventional health monitoring system which is time consuming and costly. In some instances, the new underlying device configuration is incompatible or it is impossible to update the software to restore the communication of data and so the entire health monitoring system must be replaced.

In addition, the communication of data within the health monitoring system can be interrupted due to a limitation of the technology such as one device component being out of the operating range of another device component or power source failures. In this situation, the communication of data is retried until it is received or the transmittance is terminated. As a result, the communication of data between the device components is not independent of the underlying health monitoring system infrastructure.

These issues limit the interchangeability and scalability of the device components within the health monitoring system. Therefore, there is a strong need for a cost-effective solution that overcomes the above issues by creating a highly reliable, fault tolerant and scalable health monitoring system that contains a clear communication path between device components that is completely independent of underlying architecture. The present invention addresses such a need.

SUMMARY OF THE INVENTION

A health-monitoring system and method are disclosed. In a first aspect, the health-monitoring system comprises a sensory system and a sensory to front-end communication (SFCM) protocol coupled to the sensory system. The health-monitoring system includes a front-end system coupled to the sensory system and a front-end to back-end communication (FBCM) protocol coupled to the front-end system. The health-monitoring system includes a back-end system. The SFCM protocol communicates with the front-end system using a first state awareness link and the FBCM protocol communicates with the back-end system using a second state awareness link.

In a second aspect, the method comprises providing a sensory system and coupling a sensor to front-end communication (SFCM) protocol to the sensory system. The method includes coupling a front-end system to the sensory system and coupling a front-end to back-end communication (FBCM) protocol to the front-end system. The method includes coupling the front-end system to a back-end system. The method includes communicating data between the SFCM protocol and the front-end system using a first state awareness link and communicating data between the FBCM protocol and the back-end system using a second state awareness link.

BRIEF DESCRIPTION OF THE DRAWINGS

The accompanying figures illustrate several embodiments of the invention and, together with the description, serve to explain the principles of the invention. One of ordinary skill in the art will recognize that the particular embodiments illustrated in the figures are merely exemplary, and are not intended to limit the scope of the present invention.

DETAILED DESCRIPTION OF PREFERRED EMBODIMENTS

The present invention relates to health monitoring, and more particularly, to a system and method for reliable and scalable health monitoring. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

A system and method in accordance with the present invention allows for a multiple sensory system that logically connects to a front-end system and in turn to a back-end system. These connections create a health-monitoring system with a clear data communication path that is independent of the underlying architecture of the health-monitoring system. By utilizing state awareness methods and state awareness links into the sensory, the front-end, and the back-end systems, a highly reliable and scalable health-monitoring system is achieved that can support a significant number of active users.

To describe the features of the present invention in more detail, refer now to the following description in conjunction with the accompanying Figures.

Figure 1:
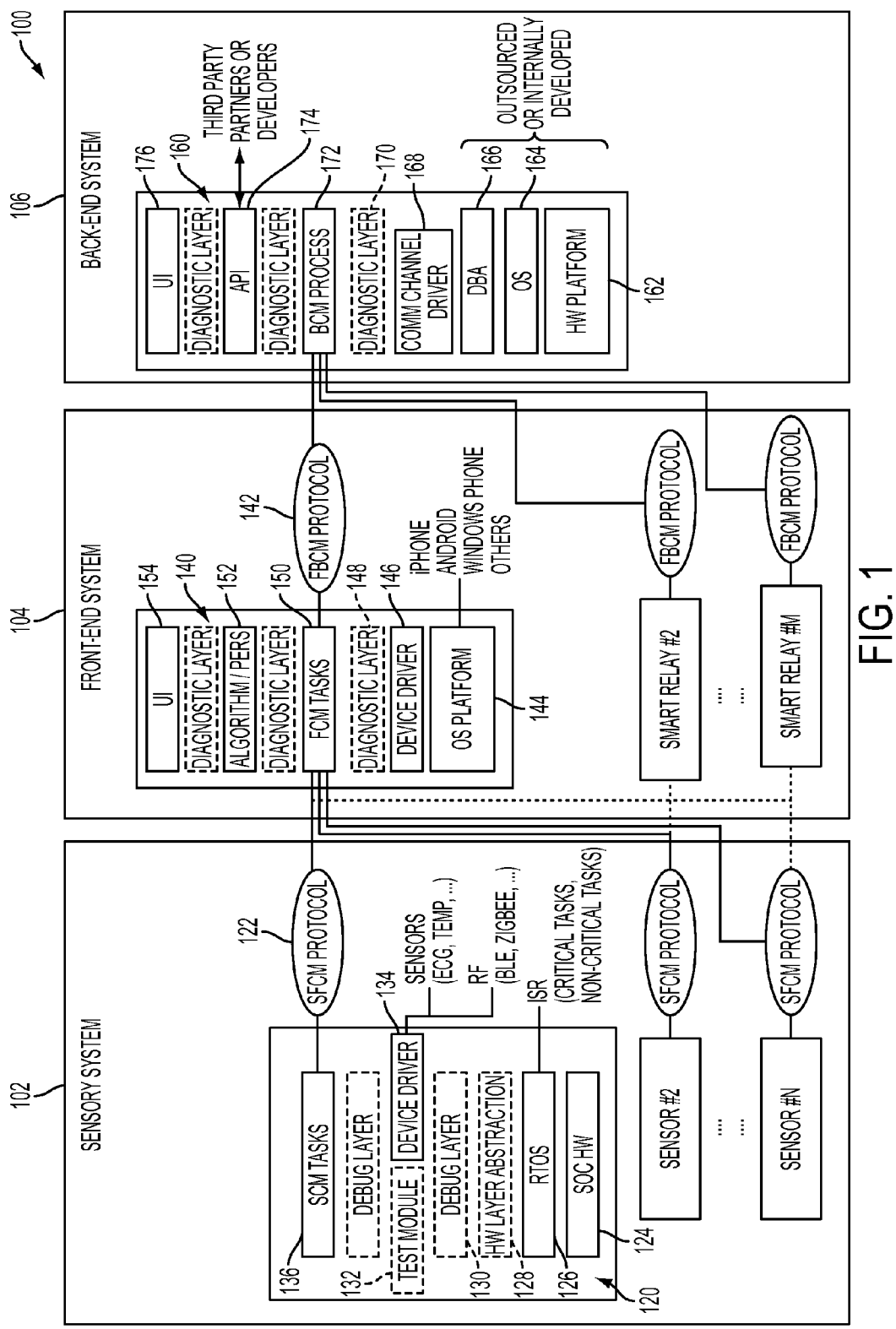
FIG. 1 illustrates a health monitoring system in accordance with an embodiment.

Health-Monitoring System:

FIG. 1 illustrates a health-monitoring system 100 in accordance with an embodiment. The health-monitoring system 100 includes a sensory system 102, a front-end system 104 coupled to the sensory system 102, and a back-end system 106 coupled to the front-end system 104. The sensory system 102 includes a sensor 120 coupled to a sensory to front-end communication (SFCM) protocol 122. The front-end system 104 includes an interface 140 coupled to a front-end to back-end communication (FBCM) protocol 142 and the back-end system 106 includes a server 160.

The SFCM protocol 122 communicates with the front-end system 104 using a first state awareness link and the FBCM protocol 142 communicates with the back-end system using a second state awareness link. These state awareness links enable each system within the health-monitoring system 100 to detect and understand the underlying architecture of each other system and reestablish communications between systems.

One of ordinary skill in the art readily recognizes that the state awareness links can detect and understand numerous types of data including but not limited to state awareness information, transmitted data and the conditions or states of both the transmitting and receiving devices. Data related to the conditions or states of both the transmitting and receiving devices includes but is not limited to information pertaining to the device types, revisions, modes and data statuses.

Device type information may include the number of physical hardware sensors present and the way in which sensory data is combined together to form a final data format. Device revision information may include the data format versions of the sensory hardware or firmware or protocol stack id. Device mode information may include retry, error recovery, data loss, normal, alert, waiting for upgrade, and require customer profile modes. Data status information may include fully encrypted data, critical data profiles or broken but recoverable data.

One of ordinary skill in the art readily recognizes that the sensor 120, the interface 140 and the server 160 can include a variety of devices including but not limited to wireless sensors, collections of body vital sign metrics in patch form, smart relays, cell phones, mobile devices, applications, and database servers and that would be within the spirit and scope of the present invention.

The sensor 120 includes a system on-a-chip hardware (SOC HW) 124, a real-time operating system (RTOS) 126, a hardware layer abstraction 128, at least one debug layer 130, a test module 132, a device driver 134, and at least one sensory communication (SCM) task 136 coupled to the SFCM protocol 122. In one embodiment, the at least one SCM task 136 includes at least one computational task. One of ordinary skill in the art readily recognizes that the SOC HW 124, the RTOS 126, the hardware layer abstraction 128, the at least one debug layer 130, the test module 132, the device driver 134 and the at least one SCM task can be coupled to each other in a variety of different ways and configurations or can be stand-alone devices and that would be within the spirit and scope of the present invention.

The interface 140 includes an operating system (OS) platform 144, a device driver 146, at least one diagnostic layer 148, at least one front-end communication (FCM) task 150 coupled to the FBCM protocol 142, a personal emergency response system (PERS) 152, and a user interface (UI) 154. The OS platform 144 can support a variety of operating systems including but not limited to independent OS platforms. One of ordinary skill in the art readily recognizes that the OS platform 144, the device driver 146, the at least one diagnostic layer 148, the at least one FCM task 150, the PERS 152, and the UI 154 can be coupled to each other in a variety of different ways and configurations or can be stand-alone devices and that would be within the spirit and scope of the present invention.

The server 160 includes a hardware (HW) platform 162, an operating system (OS) 164, a database administrator (DBA) 166, a communication (COMM) channel driver 168, at least one diagnostic layer 170, a BCM process 172 coupled to the FBCM protocol 142, an application programming interface (API) 174, and a user interface (UI) 176. The API 174 can support custom or partner user interfaces. One of ordinary skill in the art readily recognizes that that the HW platform 162, the OS 164, the DBA 166, the COMM channel driver 168, the at least one diagnostic layer 170, the BCM process 127, the API 174 and the UI 176 can be coupled to each other in a variety of different ways and configurations or can be stand-alone devices and that would be within the spirit and scope of the present invention.

Sensory System:

The RTOS 126 includes a variety of capabilities including but not limited to having no task deadlock so there is a forced timed out with logging, self-resetting for catastrophic recovery, abstracting all hardware registers so direct access of the bits/registers are not allowed, having error correction code (ECC) parity memory, and having datapath recovery. One of ordinary skill in the art readily recognizes that the RTOS 126 may include a variety of other capabilities and that would be within the spirit and scope of the present invention.

The at least one debug layer 130 includes a variety of capabilities including but not limited to having non-production code, simulating electrocardiogram (ECG), measuring temperature, resistance, Micro-Electrical Mechanical Systems (MEMS), and blood oxygen saturation, simulating RF stacks, and having an error injection module where the size target in the error injection mode is <10 Kbytes and the size target in full-mode is <64 Kbytes. One of ordinary skill in the art readily recognizes that the at least one debug layer 130 may include a variety of other capabilities and that would be within the spirit and scope of the present invention.

The SFCM protocol 122 is a two way communication protocol that pairs the sensory system 102 with the front-end system 104. The SFCM protocol 122 includes a variety of capabilities including but not limited to having a state awareness link, having the ability to miss and retry while setting up data communication paths, supporting multiple sensors, and supporting different versions of the same type of sensor. One of ordinary skill in the art readily recognizes that the SFCM protocol 122 may include a variety of other capabilities and that would be within the spirit and scope of the present invention.

Front-End System:

The at least one FCM task 150 includes a variety of capabilities including but not limited to communicating with the at least one SCM task 136 and the BCM process 172, having redundancy in the communication, operating with a fail-safe mechanism so an alarm occurs when a pairing status is unavailable or unreliable, buffering sensor data, buffering the BMC process 172 data commands, and logging location and date/time information. One of ordinary skill in the art readily recognizes that the at least one FCM task 150 may include a variety of other capabilities and that would be within the spirit and scope of the present invention.

The FBCM protocol 142 is a two way communication protocol that pairs the front-end system 104 with the back-end system 106. The FBCM protocol 142 includes a variety of capabilities including but not limited to having a state awareness link, having the ability to miss and retry while setting up data communication paths, supporting multiple physical links (SMS or data) in generic mode, and logging variable length data. One of ordinary skill in the art readily recognizes that the FBCM protocol 142 may include a variety of other capabilities and that would be within the spirit and scope of the present invention.

The device driver 146 includes a variety of capabilities including but not limited to having a physical link driver mapping layer to ensure the data communication path is independent of both the actual underlying architecture of the front-end system 104 and the OS platform 144, and having a unified payload architecture. One of ordinary skill in the art readily recognizes that the device driver 146 may include a variety of other capabilities and that would be within the spirit and scope of the present invention.

The at least one diagnostic layer 148 includes a variety of capabilities including but not limited to having non-production code, simulating the device driver 146 protocol, simulating the UI 154, simulating the at least one FCM task 150 for a higher level protocol, and having error injection. One of ordinary skill in the art readily recognizes that the at least one diagnostic layer 148 may include a variety of other capabilities and that would be within the spirit and scope of the present invention.

The UI 154 includes a variety of capabilities including but not limited to facilitating a user experience, having graphic and flow modules customized to the health-monitoring system 100, having user annotation, having a login procedure, and having its graphical display be programmable from the back-end system 106. One of ordinary skill in the art readily recognizes that the UI 154 may include a variety of other capabilities and that would be within the spirit and scope of the present invention.

Back-End System:

The BMC process 172 includes a variety of capabilities including but not limited to receiving secure data from the front-end system 104, authenticating and encrypting data and the data communication path, aggregating data, sending outbound messages, and initiating data communication path connections with the front-end system 104 or the sensory system 102. One of ordinary skill in the art readily recognizes that the BMC process 172 may include a variety of other capabilities and that would be within the spirit and scope of the present invention.

The UI 176 includes a variety of capabilities including but not limited to graphically displaying sensory or customer information, having a login procedure, having user annotation, having a user profile and account information, supporting temporary or trial periods, having an administrative procedure, and having reporting capability. One of ordinary skill in the art readily recognizes that the UI 176 may include a variety of other capabilities and that would be within the spirit and scope of the present invention.

The HW platform 162 includes a variety of capabilities including but not limited to having continuous 24/7 operation and having a redundant geographical system within and across suppliers. One of ordinary skill in the art readily recognizes that the HW platform 162 may include a variety of other capabilities and that would be within the spirit and scope of the present invention.

The OS 164 includes a variety of capabilities including but not limited to supporting independent OS platforms and the DBA 166 includes a variety of capabilities including but not limited to having independent database management architecture, being scalable, fault tolerant and distributed, and supporting millions of nodes. One of ordinary skill in the art readily recognizes that the OS 164 and the DBA 166 may include a variety of other capabilities and that would be within the spirit and scope of the present invention.

The COMM channel driver 168 includes a variety of capabilities including but not limited to supporting physical links to the front-end system 104 that are independent of the HW platform 162 and the at least one diagnostic layer 170 includes a variety of capabilities including but not limited to having isolation and simulation capability. One of ordinary skill in the art readily recognizes that the COMM channel driver 168 and the at least one diagnostic layer 170 may include a variety of other capabilities and that would be within the spirit and scope of the present invention.

Figure 2:
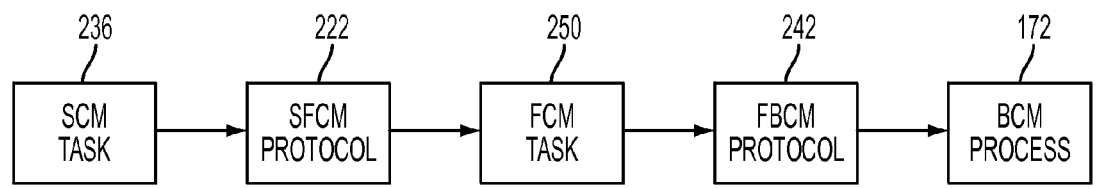
FIG. 2 illustrates a block diagram of a data communication path in accordance with an embodiment.

Data Communication Path:

The health-monitoring system 100 communicates data from the sensory system 102 to the back-end system 106 through two sets of protocols which are the SFCM protocol 122 and the FBCM protocol 142. FIG. 2 illustrates a block diagram 200 of a data communication path in accordance with an embodiment. In the block diagram 200, data is measured by the at least one SCM task 236 and communicated to the SFCM protocol 222 which connects the at least one SCM task 236 to the at least one FCM task 250.

As a result, the SFCM protocol 222 allows the at least one FCM task 250 to be aware of the state of the at least one SCM task 236 and the data measured by the underlying sensory system 102. The data is then communicated to the at least one FCM task 250, in turn to the FBCM protocol 242, and finally to the BCM process 172 to complete the data communication path from the sensory system 102 to the back-end system 106. The BCM process 172 can receive data from different paths that are created by the underlying system architectures. Therefore, the back-end system 106 is also aware of the state of both the sensory system 102 and the front-end system 104.

After the data is measured by the at least one SCM task 236, it is encrypted and secured before it is communicated to the SFCM protocol 222. As a result, the secure data is not visible to the various layers of the underlying systems within the health-monitoring system 100. One of ordinary skill in the art readily recognizes that a variety of encryption methodologies can be utilized to secure the data and that would be within the spirit and scope of the present invention.

As above described, the system and method allow for a multiple sensory system that logically connects to a front-end system and in turn to a back-end system to create a health-monitoring system with a clear data communication path that is independent of the underlying architecture of the health-monitoring system. By implementing state awareness methods and state awareness links into the sensory, the front-end, and the back-end systems, a system and method in accordance with the present invention achieves a highly reliable, fault tolerant and scalable health-monitoring system that can support a significant number of active users.

A health monitoring system and method has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk—read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A health-monitoring system comprising:
   a sensory system comprising a wireless sensor device;
   a front-end system comprising a mobile device coupled to the sensory system via a sensory to front-end communication (SFCM) protocol, wherein the SFCM protocol includes a first state awareness link that detects state information of the sensory system and the front-end system;
   a back-end system comprising a database server coupled to the front-end system via a front-end to back-end communication (FBCM) protocol, wherein the FBCM protocol includes a second state awareness link that detects state information of both the front-end system and the back-end system; and
   wherein the state information detected by the first and the second state awareness links comprises device type information, device revision information, and device mode information, further wherein the device type information includes a number of present sensors of the wireless sensor device and a final sensor data format; the device revision information includes a hardware data format version of the wireless sensor device, a firmware data format version of the wireless sensor device, and a protocol stack ID of the wireless sensor device; and the device mode information includes normal, retry, alert, data loss, error recovery, and waiting for upgrade modes.

2. The system of claim 1, wherein at least one sensory communication (SCM) task within the sensory system includes at least one task that processes the data measured by the sensory system.

3. The system of claim 2, wherein the SFCM protocol receives data from the at least one SCM task and transports the data to at least one front-end communication (FCM) task within the front-end system.

4. The system of claim 3, wherein the FBCM protocol receives the data from the at least one FCM task and transports the data to a back-end communication (BCM) process within the back-end system.

5. The system of claim 1, wherein state awareness information of the sensory system is detected and the detected state awareness information is communicated to the at least one FCM task through the first state awareness link.

6. The system of claim 1, wherein state awareness information of the front-end system is detected and the detected state awareness information is communicated to the BCM process through the second state awareness link.

7. The system of claim 6, wherein the BCM process utilizes the detected state awareness information to receive data from the at least one FCM task.

8. The system of claim 6, wherein the BCM process utilizes the detected state awareness information to message and establish a connection with either the sensory system or the front-end system.

9. The system of claim 7, wherein the BCM process receives data from communication paths that do not depend on underlying architectures of the sensory, front-end, and back-end systems.

10. The system of claim 1, wherein the SFCM protocol is a two-way communication protocol between the sensory system and the front-end system and the FBCM protocol is a two-way communication protocol between the front-end system and the back-end system.

11. A method for health-monitoring, the method comprising:
    providing a sensory system comprising a wireless sensor device;
    coupling a front-end system, comprising a mobile device, to the sensory system via a sensory to front-end communication (SFCM) protocol;
    detecting, by the front-end system, state information of the sensory system and the front-end system using a first state awareness link;
    coupling the front-end system to a back-end system, comprising a database server, via a front-end to back-end communication (FBCM) protocol;
    detecting, by the front-end system, state information of both the front-end system and the back-end system using a second state awareness link; and
    wherein the state information detected by the first and the second state awareness links comprises device type information, device revision information, and device mode information, further wherein the device type information includes a number of present sensors of the wireless sensor device and a final sensor data format; the device revision information includes a hardware data format version of the wireless sensor device, a firmware data format version of the wireless sensor device, and a protocol stack ID of the wireless sensor device; and the device mode information includes normal, retry, alert, data loss, error recovery, and waiting for upgrade modes.

12. The method of claim 11, wherein at least one sensory communication (SCM) task within the sensory system includes at least one task for processing the data measured by the sensory system.

13. The method of claim 12, further comprising:
    receiving data by the SFCM protocol from the at least one SCM task; and
    transporting the data to at least one front-end communication (FCM) task within the front-end system.

14. The method of claim 13, further comprising:
    receiving data by the FBCM protocol from the at least one FCM task; and
    transporting the data to a back-end communication (BCM) process within the back-end system.

15. The method of claim 11, further comprising:
    detecting state awareness information of the sensor system; and
    communicating the detected state awareness information to the at least one FCM task through the first state awareness link.

16. The method of claim 11, further comprising:
    detecting state awareness information of the front-end system; and
    communicating the detected state awareness information to the BCM process through the second state awareness link.

17. The method of claim 16, further comprising:
    utilizing the detected state awareness information by the BCM process to receive data from the at least one FCM task.

18. The method of claim 16, further comprising:
utilizing the detected state awareness information to message and establish a connection with either the sensory system or the front-end system.

19. The method of claim 17, further comprising:
receiving data by the BCM process from communicating paths that do not depend on underlying architectures of the sensory, front-end, and back-end systems.

20. The method of claim 11, wherein the SFCM protocol is a two-way communication protocol between the sensory system and the front-end system and the FBCM protocol is a two-way communication protocol between the front-end system and the back-end system.

* * * * *